United States Patent [19]
Beach

[11] Patent Number: 5,936,140
[45] Date of Patent: *Aug. 10, 1999

[54] METHODS OF PRODUCING FEED BY REDUCING ENDOGENOUS PROTEIN LEVELS IN SOYBEAN

[75] Inventor: Larry Ray Beach, Des Moines, Iowa

[73] Assignee: Pioneer Hi-Bred International, Inc., Des Moines, Iowa

[ * ] Notice: This patent is subject to a terminal disclaimer.

[21] Appl. No.: 08/844,314

[22] Filed: Apr. 18, 1997

Related U.S. Application Data

[63] Continuation of application No. 08/459,989, Jun. 2, 1995, abandoned.

[51] Int. Cl.$^6$ .............................. A01H 5/10; A01H 1/04; C12N 15/00
[52] U.S. Cl. .................. 800/312; 800/260; 800/278; 800/287
[58] Field of Search ..................................... 800/255, 250, 800/230, 220, 205, DIG. 26, 312, 260, 278, 265, 279, 287; 47/88; 435/69.1

[56] References Cited

PUBLICATIONS

Krebbers et al. Expression of modified seed storage proteins in transgenic plants. In:Transgenic Plants. Ed. Hiatt. Marcel Dekker, Inc. New York. pp. 37–60, 1992.

Orf and Hymowitz. Inheritance of the absence of the Kunitz inhibitor in seed protein of soybeans. Crop Sci. 19:107–109, 1979.

Tang et al. Spatial distribution of protein accumulation in soybean seed. Phytochem. 33:1289–1295, 1993.

*Primary Examiner*—Lynette R. F. Smith
*Assistant Examiner*—Melissa L. Kimball
*Attorney, Agent, or Firm*—Pioneer Hi-Bred International, Inc.

[57] ABSTRACT

The present invention provides a plant seed obtained by crossing a first plant having reduced protease inhibitor activity with a second plant that is transformed to preferentially express a preselected protein whereby the content of an endogenous protein is diminished in the seed. Also provided are a method of reducing the level of endogenous proteins and a method of producing feed.

14 Claims, No Drawings

METHODS OF PRODUCING FEED BY REDUCING ENDOGENOUS PROTEIN LEVELS IN SOYBEAN

This application is a continuation of application U.S. Ser. No. 08/459,989 filed Jun. 2,1995, now abandoned.

TECHNICAL FIELD

The present invention relates to the field of animal nutrition. Specifically, the present invention relates to methods of enhancing the nutritional content of animal feed.

BACKGROUND OF THE INVENTION

The seeds of land plants contain large quantities of storage, or reserve proteins which are synthesized during the development of the seeds. During germination and early seedling growth, these reserves are hydrolyzed to produce metabolic intermediates for use by the growing seedling. In harvested seeds, storage proteins represent an available package of condensed food and enzymes. The food value of these seeds would be increased by altering the composition of the reserve proteins to decrease the amount of undesirable proteins in the seeds.

Some of the seed storage proteins in most, if not all, plants are in a class called protease inhibitors. These inhibitors are thought to function not only as storage proteins, but as regulators of endogenous proteases, and as proteins that protect plants from insect and pathogen attack.

The plant protease inhibitors are generally low molecular weight proteins, and share in common the ability to combine with particular animal, and occasionally plant proteases, thereby abolishing the activity of these enzymes. The literature suggests that active protease inhibitors may be toxic to humans and other animals, adversely affecting the nutritional quality of plant foodstuffs. Thus, there is a need to minimize the amount of protease inhibitors in foods.

Protease inhibitors are particularly abundant in the legume family and constitute about 6% of the proteins of soybeans. See Brandon, U.S. Pat. No. 4,959,310, incorporated herein by reference. Their antinutritional nature has been linked to pancreatic hyperplasia, acinar adenoma, and overall growth reduction when raw soybean meal is fed to monogastric animals, such as chickens, rats, and quail.

Soybean (*Glycine max*) seed proteins are one example of storage proteins that are widely used in human foods such as infant formulas, tofu, soy protein isolates, soy flour, textured soy fibers and soy sauce. Soybean protein products serve as an excellent source of low cost, high quality protein for human needs. Soybeans are also widely used as a component of animal feeds. However, they must undergo costly processing to properly remove or deactivate protease inhibitors.

Soybean protease inhibitors are categorized into three classes: Kunitz trypsin inhibitors ("KTI"), Bowman-Birk inhibitors ("BBI"), and glycine-rich soybean trypsin inhibitors ("GRSTI"). The primary structure of these inhibitors consists partly of sulfur-containing (methionine and cysteine) amino acids. Killipara, K. P. and Hymowitz, T., *J. Agr. Food*, Vol. 40, pp. 2356–2363, (1992), incorporated herein by reference.

The major, predominantly expressed form of KTI's is a 21.5-KDa protein which has an inhibition specificity for trypsin. BBI is a low molecular weight (8000 kDa) protein that inhibits both trypsin and chymotrypsin simultaneously at independent reactive sites. At least ten different isoforms of BBI have been reported. GRSTI's are minor inhibitors of trypsin in soybean seed.

Various approaches have been taken to reduce the protease inhibitor content and/or activity of soybeans. These include physical (heat) and chemical treatment of soy products, as well as the genetic alteration of soybeans through conventional breeding techniques.

In any heat treatment, care must be taken because, even though heating is required to destroy the trypsin inhibitors, improper heating will result in damage to the protein product itself. Furthermore, although the protease inhibitor activity is largely inactivated by denaturation through conventionally applied heat treatment of soy flour, 10–15% residual activity usually remains. The unusual structure of BBI is the most likely reason for this residual activity. BBI is strongly cross-linked by disulfide bonds which gives the molecule resistance to heat denaturation. Thus, heat treatment of seed or soy products to reduce inhibitor expression is not completely successful and furthermore, involves costly energy usage.

The solvent-extraction method is another process used to eliminate protease inhibitors from raw soybeans. This chemical extraction, while removing the various inhibiting materials, results in considerable loss of the oil in the seed, thus reducing its food value. At the same time, the solvent poses problems of cleanup and disposal.

Genetic modification of the soybean plant to develop low inhibitor activity varieties has also been proposed, but has inherent limitations. Desirable nutritional value may be lost concomitant with reduction of the inhibitors, and cross pollination of the genetic variant with another cultivar could result in reexpression of the protease inhibitor gene. Further, altering expression of one inhibitor may not affect the expression of another.

As yet, conventional breeding and tissue culture technology have been unable to produce a soybean plant,with low levels of protease inhibitors, although a need exists for such plants. Breeders have attempted to use genes lacking KTI due to mutations of the gene. See e.g. Zhang, et al., "Effects of Extrusion and Expelling on the Nutritional Quality of Conventional and Kunitz Trypsin Inhibitor-Free Soybeans"; *Poultry Science*, Vol. 72; pp. 2299–2308; (1993); incorporated herein in its entirety by reference. It is known that KTI-free soybean has a genetic difference which results in a 40 to 50% decrease in trypsin inhibitor activity. See e.g. Friedman, et al., *J. Agric. Food* Chem.; Vol. 39; pp. 327–335; (1991); and Anderson-Hafermann, et al., *Poultry Sci.*; Vol. 71; pp. 1700–1709; (1992); both incorporated herein in their entirety by reference. However, although the aforementioned reductions in levels of protease inhibitors ("PI") is unprecedented and significant, the levels are not low enough to completely eliminate the need to inactivate the remaining PI for animal feed. Since the PI in soybean, for example, are contributed from three different classes of inhibitors and each of these classes is comprised of proteins coded by multiple genes, there are no known means to genetically alter all classes of PI with a common method.

Until now, only one method has been illustrated to result in the reduction of all protease inhibitors in the plant seeds. The method referred to is the introduction of a foreign gene from Brazil nut encoding higher levels of methionine-rich 2S seed storage protein such as Brazil nut protein ("BNP"). Altenbach, et al., *Plant Mol. Biol.*, Vol. 8; pp. 239–250; (1987); incorporated herein in its entirety by reference. The introduction of the BNP gene resulted in a 60% reduction in overall trypsin inhibitor activity and a 90% reduction in overall α-chymotrypsin inhibitor activity. However, the reduction in levels of protease inhibitors is still not sufficient.

Based on the foregoing, there is a need to provide plant seeds and feed products that would not need processing before feeding to monogastric animals and/or humans.

It is therefore an object of the present invention to provide a novel method to eliminate or reduce the content of endogenous proteins in plant seeds.

It is a further object of the present invention to provide plant seeds that do not require time consuming or costly processing to eliminate protease inhibitor activity.

It is a further object of this invention to provide a transgenic plant that produces a seed having little or no protease inhibitor content.

SUMMARY OF THE INVENTION

In accordance with these objectives, the present invention provides a plant seed that is genetically modified, relative to a wild type of the species of the seed, to preferentially express a preselected protein whereby the content of other endogenous proteins is diminished in the seed. The plant seed is further modified to have reduced levels of trypsin and/or chymotrypsin inhibitor activity. The preselected protein is preferably a methionine-rich 2S seed storage protein, Brazil nut protein ("BNP").

The invention is based on the discovery that the combination of the traits of BNP and reduced levels of KTI, BBI and/or GRSTI into the same cultivar leads to an unexpectedly high reduction or elimination of inhibitor activity in the seed. Thus, the present method eliminates the need for costly processing which can damage protein products.

DETAILED DESCRIPTION OF THE INVENTION

The present invention is based on the surprising discovery that a combination of the traits of BNP and reduced levels of KTI, BBI and/or GSTI in the same cultivar results in the reduction or elimination of antinutritional protease inhibitors in the seed, thus eliminating or reducing the need to further process the seed-based foodstuffs to effectuate a reduction in content. The prior art provides no indication that the overexpression of a protein such as BNP should reduce the expression of the GSI and/or KTI because these sequences are not unusually rich in sulfur-containing amino acid. It is therefore not predicted that a cross of a seed without KTI with BNP-expressing seed would have levels of PI at or near zero.

As used herein, "genetically modified" means a plant cell stably incorporating a nucleic acid construct introduced by transformation methods. The term "wild type" refers to an untransformed cell.

As used herein, "rich" means containing a higher percentage of amino acid than the average protein.

The invention also embraces reducing translation of nucleic acid sequences encoding endogenous proteins. "Endogenous" protein refers to the native protein normally found in its natural location in the plant. In addition, the invention comprises the methods of preparing and using the various DNA constructs of the present invention. Plants, seeds, and microorganisms transformed with the nucleic acid sequences described are also embodiments of the invention.

Preferred plants that produce seeds wherein protein content may be improved by this method include, but are not limited to, soybeans, canola, corn, sunflower, wheat, barley, oats, millet, rice, sorghum and rye. The seeds may be used directly as feed or food. The most preferred plant seed is *Glycine max*.

This invention provides a simple, rapid, and reliable process for the production of transgenic soybean plants with reduced protease inhibitor activity in the resulting seeds. The method is genotype independent and shows a substantial improvement over previously-used systems because it eliminates or considerably reduces necessary, time-consuming, and costly steps, such as toasting, to eliminate protease inhibitor activity from soy food products.

As used herein, "promoter" refers to a DNA sequence in a gene, usually upstream (5') to its coding sequence, which controls the expression of the coding sequence by providing the recognition for RNA polymerase and other factors required for promoter transcription. Preferred promoters are those that allow expression of the preselected protein specifically in seeds to avoid any potential deleterious effect in non-seed organs. Examples of seed specific promoters include, but are not limited to, the promoters of seed storage proteins which express these proteins in a highly regulated manner. Thompson, et al., *BioEssays*; Vol. 10; pp. 108–113; (1989); incorporated herein in its entirety by reference. Several seed specific promoters for expression of proteins in seeds of dicotyledonous plants that are of particular use include bean β-phaseolin, napin, β-conglycinin, and soybean lectin. For monocotyledonous plants, maize 15 kD zein, 22 kD zein, γ-zein, waxy, globulin 1, shrunken 1, and shrunken 2 promoters will be particularly useful to produce expression of peptides. Those skilled in the art will recognize other promoters as well that will provide constructs for increased levels of the preselected protein in the plant chosen for transformation.

The most preferred preselected protein is BNP. Altenbach, et al., *Plant Mol. Biol.*; Vol. 8; pp. 239–250; (1987); incorporated herein in its entirety by reference. A natural or constructed DNA or RNA sequence encoding this protein is introduced into plant cells by any method of transformation that stably incorporates the gene into the plant genome. This can include a variety of vectors, such as viral vectors, episomal vectors, shuttle vectors, Ti plasmid vectors and the like, all in accordance with standard procedures. Sun, et al., European Patent Application No. EP 295,959; (1991); incorporated herein in its entirety by reference. A "vector" is a replicon, such as a plasmid, cosmid or bacteriophage, to which another DNA segment may be attached so as to bring about replication of the attached segment, or to allow its introduction into a cellular host.

As used herein with respect to a protein, the term "heterologous" means that the gene or gene fragment encoding the protein is obtained from one or more sources other than the genome of the species of plant within which it is ultimately expressed. The source can be natural, e.g., the gene can be obtained from another source of living matter, such as bacteria, yeast, fungi and the like, or a different species of plant. The source can also be synthetic, e.g., the gene or gene fragment can be prepared in vitro by chemical synthesis.

As used herein with respect to a preselected protein, the term "expresses" means that the gene encoding this protein is stably incorporated into the genome of the cells, so that the product encoded by the gene, e.g., a methionine-rich protein such as Brazil nut protein (BNP), is produced within the cells. For example, novel plants resulting from expression of BNP, contain extractable seed BNP levels of about 10% of the seed protein. Furthermore, as a result of BNP expression, the endogenous protein levels are diminished at least about 50% or preferably at least about 10%, most preferably completely diminished. Those skilled in the art will recognize that the levels of extractable protein necessary to reduce endogenous protein levels may vary since different proteins will contain different levels of the desired amino acid residues.

Levels of an endogenous protein in a plant seed are reduced by the use of nucleic acid sequences inserted into the genome of a plant to cause the expression of a preselected protein, the sequence of which requires a limiting amino acid necessary to construct the primary structure of the endogenous protein. Synthesis of the preselected protein removes the source of the amino acid for synthesis of the endogenous protein, thus inhibiting its synthesis and subsequent presence in the seed. The amount of inhibition of the endogenous protein will depend on the location in the genome and the number of copies of the heterologous gene in the genetically-modified cell. These will affect expression of the preselected protein. Transgenic plants will exhibit a variety of different phenotypic expression of the preselected protein, and selecting plants with high levels of expression can be readily achieved by skilled artisans in accordance with the present invention.

The properties of the nucleic acid sequences encoding the preselected protein may be varied and the preferred embodiment describes a number of features which may be advantageous but that a person skilled in the art will recognize as not being absolutely essential. These include the selection of a particular construct and vector to introduce the sequence into the cell and produce expression of the protein. A skilled artisan can construct an expression cassette adequate for expression of the preselected protein in the chosen cellular system with no undue experimentation. The heart of the invention is the level of expression of the preselected protein; therefore, additional copies of the nucleic acid sequence will normally result in increased inhibition of synthesis of the endogenous protein.

By way of example, and not limitation, those skilled in the art will readily appreciate that additional proteins may be substituted for the BNP protein as the preselected seed protein. The skilled artisan will recognize that choice of the preselected protein will be based on the amino acid composition of the protein and its ability to accumulate in seeds. This includes all classes of seed storage proteins; the 2S, 7S, and 11S proteins with or without modification to increase the content of the designated amino acid in the protein. The amino acid can be chosen for its nutritional value to produce a value-added trait to the plant as well as its purpose as a sink to limit availability to the designated endogenous protein. Examples of suitable sources for protein sequences usable in accordance with the present invention are plants, in particular higher plants. Amino acids desirable for value-added traits as well as a source to limit synthesis of an endogenous protein include, but are not limited to methionine, cysteine, glycine, lysine, tryptophan, and tyrosine.

As used herein, "plant" refers to either a whole plant, a plant part, a plant cell, or a group of plant cells. The class of plants which can be used in the method of the invention is generally as broad as the class of seed-bearing higher plants amenable to transformation techniques, including both monocotyledonous and dicotyledonous plants. The transformation of the plants in accordance with the invention may be carried out in essentially any of the various ways known to those skilled in the art of plant molecular biology. These include but are not limited to particle bombardment, microinjection, electroporation, and Agrobacterium-mediated DNA transfer.

Following transformation, regeneration will normally be involved in obtaining a whole plant from the transformation process. Techniques for regenerating plants from tissue culture, such as transformed protoplasts or callus cell lines, are known in the art. See, e.g., Phillips, et al., *Plant Cell Tissue Organ Culture*; Vol. 1; p. 123; (1981); Patterson, K. E. and N. P. Everett; *Plant Sci.*; Vol. 42; pp. 125–132; (1981); Wright, et al., *Plant Cell Reports*; Vol. 6; pp. 83–89; (1987); Barwale, et al., *Planta*; Vol. 167 pp. 473; (1986); all incorporated herein in their entirety by reference. The selection of an appropriate method is within the skill of the art.

Examples of the practice of the present invention detailed herein relate specifically to soybean plants and expression vectors operable in dicots. Soybean was chosen as a model system for these examples primarily because of the present capability to regenerate soybean plants from transformed individual soybean cells in a manner now known in the art. The expression vectors utilized herein are demonstrably capable of operation in cells of many dicotyledonous plants both in tissue culture and in whole plants. The invention disclosed herein is thus operable in dicotyledonous species to transform individual plant cells and to achieve full, intact plants in dicot plant species which can be regenerated from transformed plant calli and which express preselected seed proteins. For those species not presently regenerable, the present invention is fully operable when the techniques for such regeneration become developed.

In addition, chimeric expression vectors involving seed proteins are also known and have been described in the literature which have been demonstrated to be operable in cells of monocots, at least in tissue culture. It is reasonable then to expect that these vectors will also be operable in whole monocot plants when the techniques for regenerating these plants are perfected so that any preselected seed protein can be expressed in any monocotyledonous plant seed. The present invention is thus applicable to monocots as well as to dicots.

Therefore, practice of this invention can be used to improve crop plants like rice, maize, wheat, and barley with few modifications. An example of such an embodiment would be the introduction of a high lysine derivative of α-hordothionin into a barley or wheat cell to reduce the purothionin content of the seed and increase its lysine content.

Thionins are small antimicrobial proteins present in the endosperm of barley, wheat, and other plant species. Florack, et al., *Plant Mol. Biol.*; Vol. 24; pp. 83–96; (1994); incorporated herein in its entirety by reference. Native α-hordothionin is rich in arginine and lysine residues, containing five residues (10%) of each. Several derivatives of this protein have been made in which other amino acids were replaced with lysine to produce a compound less toxic to fungi and significantly more enriched with lysine (29% lysine).

Purothionins are also small, lysine-rich proteins in the endosperm of wheat and several other species of Gramineae. Wada, K., *Plant & Cell Physiol.*; Vol. 23(8); pp. 1357–1361; (1982); incorporated herein in its entirety by reference. Purothionins are lethal to brewer's yeast and, as a result, barley or wheat with high levels of these proteins cannot be used for making high quality beers.

However, according to this invention, a high-lysine α-hordothionin or another genetically-engineered thionin designed for lysine enrichment and reduced toxicity to microorganisms could be used to decrease the levels of purothionins and increase the lysine content of barley, wheat, or other graminaceous plants. The lysine-enriched residue could be sold for feed following the brewing process.

The foregoing is one description of the scope of the invention and a skilled artisan will recognize many other examples of plant improvement to which the invention can be applied.

The present invention can be better understood by reference to the following more detailed example which illustrates its various applications, but is in no way intended to limit the scope thereof.

Experimental

Transformation of *Glycine max* with a Methionine-rich Seed Storage Protein

Plant Transformation

Soybean (*Glycine max*) seed, Pioneer variety 9341, was surface sterilized by exposure to chlorine gas evolved in a glass bell jar. Gas was produced by adding 3.5 ml hydrochloric acid (34–37% w/w) to 100 ml sodium hypochlorite (5.25% w/w). Exposure was for 16–20 hours in a container approximately one cubic foot in volume. Surface sterilized seed was stored in petri dishes at room temperature. Seed was germinated by plating on 1/10 strength agar solidified medium according to Gamborg [B5 basal medium with minimal organics, Sigma Chemical Co., cat. no. G5893, 0.32 gm/L; sucrose, 0.2% w/v and 2-[N-morpholino] ethanesulfonic acid (MES), 3.0 mM] without plant growth regulators and culturing at 28° C. with a 16 hour day length and cool white fluorescent illumination of approximately 20 mEm2S1. After three or four days, seed could be prepared for cocultivation. The seed coat was removed and the elongating radical was removed 3–4 mm below the cotyledons. Ten prepared seeds were held in each of several petri dishes.

Construction of plasmids

For the construction of a plasmid containing four copies of the methionine-rich protein gene, the plasmid pD3-8-12 (Altenbach, et al., *Plant Mol. Biol.*; Vol. 13, pp. 513–522; (1989); incorporated herein in its entirety by reference) was used as the starting point. The BNP gene was excised from pD3-8-12 by digestion with Eco R1, Hind III, and Xmn 1. The ends of the fragment were made blunt with the Klenow fragment of DNA polymerase, and a 3 kb fragment containing the chimeric gene was gel-purified. This fragment was ligated to the plasmid pD3-8-12 which had been digested with Sma 1 and treated with calf intestinal phophatase. The resulting plasmid, called pD3-8-12-2X, contained two copies of the chimeric methionine-rich BNP gene in tandem array.

To produce the plasmid containing four copies of the chimeric gene, the pD3-8-12-2X plasmid was digested with Eco R1 and Hind III and the ends were made blunt with the Klenow fragment of DNA polymerase. A 6 kb fragment containing two copies of the chimeric gene was isolated. This fragment was ligated to the plasmid pD3-8-12-2X which had been digested with Sma I and treated with calf intestinal phosphatase. The resulting plasmid is pD3-8-12-4X.

The chimeric BNP genes were then inserted into the Ti plasmid vector pARC12. A 12 kb fragment from pD3-8-12-4X was excised by digestion with Eco R1 and Hind III and ligated to pARC12 which had been digested with Eco R1 and Hind III. The resulting plasmid, p12-4X, contains four copies of the BNP gene between the tDNA borders, as well as a chimeric nopaline synthase-neomycin phosphotransferase II gene for selection in plant cells. The plasmid was then transferred from *E. coli* to *Agrobacterium tumefaciens* strain LBA 4404 by triparental mating. The identities of the resulting bacteria were confirmed by southern blot analysis.

Preparation of *Agrobacterium tumefaciens* LBA4404/p12GUSBN17 and p12-4X

Overnight cultures of *Agrobacterium tumefaciens* strain LBA 4404 harboring the binary plasmid p12-4X (DP1813, four copies BNP sequence), grown to log phase in Minimal A medium containing tetracycline, 1.0 mg/ml, were pooled and an optical density measurement at 550 nm was taken. Sufficient volume of the culture was placed in 15 ml conical centrifuge tubes such that upon sedimentation between 1.0 and $2.0 \times 10^{10}$ cells were collected in each tube, where O.D.550 $1.0 = 1.4 \times 10^9$ cells/ml. Sedimentation was by centrifugation at 6000 g for 10 minutes. After centrifugation the supernatant was decanted and the tubes were held at room temperature until inoculum was needed but not longer than one hour.

Transformation

Inoculations were conducted in batches such that each plate of seed was treated with a newly resuspended pellet of Agrobacterium. One at a time the pellets were resuspended in 20 ml inoculation medium. Inoculation medium consisted of B5 salts (G5893), 3.2 gm/L; sucrose, 2.0% w/v. 6-benzylaminopurine (BAP), 44 mM; indolebutyric acid (IBA), 0.5 mM; acetosyringone (AS), 100 mM and was buffered to pH 5.5 with MES, 10 mM. Resuspension was by vortexing. The inoculum was then poured into a petri dish containing prepared seed and the cotyledonary nodes were macerated with a surgical blade. This was accomplished by dividing seed in half by longitudinal section through the shoot apex preserving the two whole cotyledons. The two halves of the shoot apex were then broken off their respective cotyledons by prying them away with a surgical blade. The cotyledonary node was then macerated with the surgical blade by repeated scoring along the axis of symmetry. Care was taken not to cut entirely through the explant to the abaxial side. Twenty explants were prepared in roughly five minutes and then incubated for 30 minutes at room temperature without agitation. Additional plates were prepared during this time. After 30 minutes the explants were transferred to plates of the same medium solidified with Gelrite (Merck & Co., Inc.), 0.2% w/v. explants were embedded with the adaxial side up and level with the surface of the medium and cultured at 22° C. for three days under cool white fluorescent light, approximately 20 $mEm^2S^1$.

Culture and Selection

After three days the explants were moved to liquid counterselection medium. Counterselection medium consisted of B5 salts (G5893), 3.2 gm/L; sucrose, 2.0% w/v; BAP, 5.0 mM ; IBA, 0.5 mM; vancomycin, 200 mg/ml; cefotaxime, 500 mg/ml and was buffered to pH 5.7 with MES, 3 mM. Ten explants were washed in each petri dish with constant, slow gyratory agitation at room temperature for four days. Counterselection medium was replaced four times.

The explants were then picked to agarose solidified selection medium. Selection medium consisted of B5 salts (G5893), 3.2 gm/L; sucrose, 2.0%, w/v; BAP, 5.0 mM; IBA, 0.5 mM; kanamycin sulfate, 50 mg/ml; vancomycin, 100 mg/ml; cefotaxime, 30 mg/ml; timentin, 30 mg/ml and was buffered to pH 5.7 with MES, 3.0 mM. Selection medium was solidified with SeaKem agarose, 0.3% w/v. The explants were embedded in the medium, adaxial side down and cultured at 28° C. with a 16 hour day length and cool white fluorescent illumination of 60–80 $mEm^2S^1$.

After two weeks explants were again washed with liquid medium on the gyrotory shaker. This time the wash was conducted overnight in counterselection medium containing kanamycin sulfate, 50 mg/ml. The following day explants were picked to agarose solidified selection medium. Again they were embedded in the medium, adaxial side down, Culture was as before for another two week period.

Regeneration

After one month on selective media transformed tissue became visible as green sectors of regenerating tissue against a background of bleached, less healthy tissue. Explants without green sectors were discarded, explants with green sectors were transferred to elongation medium. Elongation medium consisted of B5 salts (G5893), 3.2 gm/L; sucrose, 2.0% w/v; IBA, 3.3 mM; gibberellic acid, 1.7 mM; vancomycin, 100 mg/ml; cefotaxine, 30 mg/ml; and timentin, 30 mg/ml, buffered to pH 5.7 with MES, 3.0 mM. Elongation medium was solidified with gelrite, 0.2% w/v. They were embedded adaxial side up and cultured as before. Culture was continued on this medium with transfers to fresh plates every two weeks. When shoots became 0.5 cm in length they were excised at the base and placed in rooting medium in 13×100 mm test tubes. Rooting medium consisted of B5 salts (G5893), 3.2 gm/L; sucrose, 15 gm/L; nicotinic acid, 20 mM; pyroglutamic acid (PGA), 900 mg/L and IBA, 10 mM. It was buffered to pH 5.7 with MES, 3.0 mM and solidified with Gelrite, 0.2% w/v. After ten days the shoots were transferred to the same medium without IBA or PGA. Shoots were rooted and held in these tubes under the same environmental conditions as before.

When a root system was well established the plantlet was transferred to sterile soil mix in plant cons (ICN Biomedicals, Inc., cat. no. 26-720 & 1-02). Temperature, photoperiod and light intensity remained the same as before, Under these conditions the regenerates became vigorous, mostly normal (though small) plants. When their root systems again became well established a corner of the plant con was cut off and the plants were gradually hardened off in an environmental chamber or greenhouse. Finally they were potted in soil mix and grown to maturity, bearing seed, in a greenhouse.

Growth, Increase, and Harvest of Transgenic Soybeans.

Seed from untransformed and transformed plants of the same variety (9341) was planted in the spring of 1992 and harvested in the fall of 1992 in Iowa. Each individual line was kept separate while grown in one or more 10.5 foot rows for maximum increase. Lines in which four copies were inserted are designated BNP4X.

Most of the harvested BNP4X seed in the fall of 1992 was increased in Puerto Rico. This seed was planted by line in December, 1992 and harvested by line in March, 1993.

Part of the increased, harvested seed was returned for yield test and further laboratory testing. The rest was replanted by line in March, 1993 and harvested by line in June, 1993 in Puerto Rico. The entire second cycle increase was about 2 acres, or a little more than 0.1A per line.

Crossing of BNP Line with the Public Variety "Kunitz"

An experimental BNP line, BX4P9341B6, was crossed by the public variety "Kunitz". BX4P9341B6 was chosen as one parent because it contained the gene from Brazil nut that was responsible for elevated expression of methionine and reduction in the expression of indogenous protease inhibitors. Kunitz was chosen as the other parent because it also exhibits reduced expression of protease inhibitors. It was thought that by crossing these two lines, we could select experimental lines that contained the BNP gene, expressed reduced levels of protease inhibitors and produced a higher percentage of methionine in the protein.

During the summer of 1993, BX4P9341B6 and Kunitz were planted in the breeding nursery at Johnston and crosspollinated to produce $F_1$ seed. Following the harvest of the $F_1$ seed at Johnston, several seed were sent to the Pioneer Hi-Bred International, Inc. winter nursery facility in Salinas, Puerto Rico for 2-cycle advance. The $F_1$ seed were space planted under lights to control the photoperiod and allow the plants to produce more seed per plant than would be produced under normal planting conditions. At maturity, the $F_2$ seed from each $F_1$ plant were harvested individually and placed in envelopes to maintain the identity of the seed from individual $F_1$ plants. Next, the $F_2$ seed from each $F_1$ plant were space planted in rows under artificial lights to allow for maximum seed production. At maturity, an equal number of $F_2$ plants were harvested from each row and threshed individually to maintain the identity of each line. Experimental lines were then shipped to Johnston, Iowa.

During the summer of 1994, seed from 400 experimental lines was grown in a short row approximately 3' in length for seed increase. The seed increase was needed in order to obtain enough seed for lab testing. The parental lines were also planted in order to determine differences between the experimental lines and parental lines. Following harvest during the fall of 1994, seed from experimental lines and parental lines were tested for BNP content and level of protease inhibition.

The genetics of the BNP gene from Brazil nut was determined to be inherited as a single dominant gene so it was calculated that approximately 100 experimental lines out of the 400 lines tested should breed true or be homozygous for this trait. The Kunitz gene was determined by Hymowitz et al. to be inherited as a single recessive so approximately 100 experimental lines of the original 400 should be homozygous for this trait. Since both genes assort independently of each other, it was determined that approximately 25 lines should be true breeding for both traits. With this in mind, experimental lines were tested for presence of BNP and for a reduction in protease inhibitors, mainly trypsin and chymotrypsin inhibitor activity.

Spectrophometric analysis of trypsin and chymotrypsin inhibitor activities in soybean seeds were carried out according to the published methods of Hymowitz, et al., *J. Agr. Food*; Vol. 40; pp. 2356–2363; (1992); incorporated herein in its entirety by reference. Analyses of trypsin inhibitor activity/gram (TIU/gram) and α-chymotrypsin inhibitor activity/gram (CIU/gram) were undertaken.

The amino acid content of seeds from transformed and untransformed plants was analyzed by methods described in the *Official Methods of Analysis of the AOAC*; Hilrich, K. (ed.); AOAC International; Vol. 2; pp. 1096–1097, (1990); incorporated herein in its entirety by reference.

Table 1 illustrates the level of trypsin inhibitor activity of W6383-014, an experimental line developed at Pioneer that expresses reduced level of trypsin inhibitor activity; Kunitz, a cultivar developed at the University of Illinois Agricultural Experiment Station which also expresses reduced levels of trypsin inhibitor activity; four BNP lines (BX4P9341B6, BX4P9341C7, BX4P9341C5, and BX4P9341C2) that express increased levels of methionine in the seed protein; and Pioneer brand 9341, a commercial cultivar that was the original recipient of the BNP gene. It can be noted from Table 1 that Kunitz expresses lower levels of trypsin inhibitor activity than the commercial cultivar 9341. Also, the BNP lines express trypsin inhibitor levels that are significantly lower than either Kunitz or 9341. This reduction in trypsin inhibitor activity of the BNP lines below Kunitz was determined to be a source-sink relationship for sulfur since both methionine and some protease inhibitors are sulfur-containing compounds.

Table 2 illustrates the difference in chymotrypsin activity between the same cultivars as mentioned in the previous paragraph. The level of chymotrypsin inhibitor activity/ gram in the BNP lines in approximately one-half that of Kunitz and 9341. This level of reduction has only been seen in wild relative species of soybean, *Glycine tomentella*.

Table 3 illustrates the level of trypsin activity (TIU/gram) of 80 experimental lines from the cross of BX4P9341B6 and "Kunitz". These lines were selected from the original set of 400 experimental lines because they were homozygous for either the presence of absence of the BNP trait and represented the 2 extreme levels of trypsin inhibitor activity for presence and absence of BNP. Under the BNP column, a "9" means that all seed tested contained the BNP trait; a "1" means that all seed tested lacked the BNP trait. It can be noted in Table 3 that lines containing the BNP trait expressed lower levels of trypsin inhibitor activity than lines lacking the trait. In comparing Tables 1 and 3 it can also be noted that there are several experimental lines that contain the BNP trait and express trypsin inhibitor activity levels significantly lower than the BNP parent, BX4P9314B6. Since 25 out of the original 400 experimental lines should contain both the BNP trait and reduced trypsin inhibitor activity, several lines were assigned genotype designations of ti/ti which denotes reduced trypsin inhibitor activity. These lines are believed to contain the trait from Kunitz that is responsible for the reduction in trypsin inhibitor activity.

Table 4 illustrates the correlation between BNP, TIU/gram and CIU/gram. It is significant that there is a negative correlation between BNP and TIU/gram (−0.8428) and also BNP and CIU/gram (−0.7170). These correlations mean that when BNP is present, trypsin inhibitor activity levels and chymotrypsin inhibitor activity levels are reduced. There is also a positive correlation between TIU/gram and CIU/gram (0.7443), which means that as trypsin inhibitor activity levels are reduced so are chymotrypsin inhibitor activity levels. It can be further deduced that the presence of BNP reduces both trypsin inhibitor activity and chymotrypsin inhibitor activity.

Table 5 illustrates the results for the amino acid analysis of 10 experimental lines, 9341, Kunitz and BX4P9341B6. Table 5 indicates that BX4P9341B6 contains a higher methionine (METI) content than either Kunitz, 9341 or the 10 experimental lines that were determined to lack the BNP trait (BNP score of 1). Also, there are a few experimental lines that were determined to contain the BNP trait and express methionine levels above the BNP parent BX4P9341B6.

The above data indicates that it is possible to obtain an experimental line containing the BNP trait expresses trypsin inhibitor levels below the cultivars Kunitz or BX4P9341B6, and expresses higher levels of methionine content than current commercial cultivars.

TABLE 1

COMPARISON OF PARENTAL LINES FOR TIU/GRAM

| VARIETY | W6383-014 | KUNITZ | BX4P9341B6 | BX4P9341C7 | BX4P9341C5 | BX4P9341C2 | P9341 |
|---|---|---|---|---|---|---|---|
| REP 1 | 1953.13 | 2246.09 | 1123.05 | 1074.22 | 1025.39 | 1269.53 | 3076.17 |
| REP 2 | 2880.86 | 2734.38 | 976.56 | 1123.05 | 781.25 | 781.25 | 2734.38 |
| REP 3 | 2392.58 | 1757.81 | 1123.05 | 878.91 | 927.73 | 976.56 | 3027.34 |
| REP 4 | 2929.69 | 1806.64 | 927.73 | 683.59 | 878.91 | 830.08 | 2929.69 |
| REP 5 | 2050.78 | 2001.95 | 1464.84 | 830.08 | 830.08 | 1416.02 | 2734.38 |
| REP 6 | 3027.34 | 1953.13 | 1416.02 | 927.73 | 1074.22 | 1123.05 | 3369.14 |
| REP 7 | 2294.92 | 2587.89 | 1269.53 | 1367.19 | 1367.19 | 1367.19 | 3076.17 |
| REP 8 | 2685.55 | 1953.13 | 781.25 | 976.56 | 634.77 | 1123.05 | 2685.55 |
| REP 9 | 2246.09 | 2539.06 | 1513.67 | 1660.16 | 1269.53 | 1269.53 | 2783.20 |
| SUM | 22460.94 | 19580.08 | 10595.70 | 9521.48 | 8789.06 | 10156.25 | 26416.02 |
| AVERAGE | 2495.66 | 2175.56 | 1177.30 | 1057.94 | 976.56 | 1128.47 | 2935.11 |
| LSD = 262.54 | | | | | | | |

TABLE 2

COMPARISON OF PARENTAL LINES FOR CIU/GRAM

| VARIETY | W6383-014 | KUNITZ | BX4P9341B6 | BX4P9341C7 | BX4P9341C5 | BX4P9341C2 | P9341 |
|---|---|---|---|---|---|---|---|
| REP 1 | 100.00 | 103.00 | 49.00 | 46.00 | 28.00 | 40.00 | 102.00 |
| REP 2 | 67.00 | 67.00 | 32.00 | 42.00 | 37.00 | 40.00 | 65.00 |
| REP 3 | 63.00 | 62.00 | 30.00 | 29.00 | 33.00 | 31.00 | 59.00 |
| REP 4 | 70.00 | 73.00 | 32.00 | 45.00 | 49.00 | 37.00 | 74.00 |
| REP 5 | 74.00 | 73.00 | 46.00 | 38.00 | 40.00 | 52.00 | 76.00 |
| REP 6 | 84.00 | 86.00 | 76.00 | 59.00 | 64.00 | 57.00 | 86.00 |
| REP 7 | 83.00 | 89.00 | 54.00 | 50.00 | 51.00 | 36.00 | 86.00 |
| REP 8 | 55.00 | 61.00 | 31.00 | 21.00 | 28.00 | 29.00 | 58.00 |
| REP 9 | 59.00 | 65.00 | 39.00 | 42.00 | 45.00 | 34.00 | 82.00 |
| SUM | 655.00 | 679.00 | 389.00 | 372.00 | 375.00 | 356.00 | 688.00 |
| AVERAGE | 72.78 | 75.44 | 43.22 | 41.33 | 41.67 | 39.56 | 76.44 |

TABLE 3

SPECTROPHOTOMETRIC ANALYSIS OF TRYPSIN INHIBITOR ACTIVITY (TIU/GRAM) AND CHYMOTRYPSIN INHIBITOR ACTIVITY (CIU/GRAM) OF EXPERIMENTAL LINES FROM THE CROSS BX4P9341B6/KUNITZ

| EXPT'L | TIU | TIU/GRAM | BNP (9/1) 9 = +, 1 =− | TRYPSIN GENOTYPE | CIU/ GRAM |
|---|---|---|---|---|---|
| 8 | 60.0 | 2929.7 | 1 | Ti/Ti | 97 |
| 200 | 58.0 | 2832.0 | 1 | Ti/Ti | 74 |
| 279 | 56.0 | 2734.4 | 1 | Ti/Ti | 57 |
| 17 | 55.5 | 2710.0 | 1 | Ti/Ti | 106 |
| 327 | 55.0 | 2685.5 | 1 | Ti/Ti | 66 |
| 224 | 54.5 | 2661.1 | 1 | Ti/Ti | 68 |
| 191 | 53.0 | 2587.9 | 1 | Ti/Ti | 73 |
| 349 | 52.5 | 2563.5 | 1 | Ti/Ti | 61 |
| 273 | 51.0 | 2490.2 | 1 | Ti/Ti | 57 |
| 164 | 49.5 | 2417.0 | 1 | Ti/Ti | 72 |
| 271 | 49.5 | 2417.0 | 1 | Ti/Ti | 58 |
| 136 | 48.5 | 2368.2 | 1 | Ti/Ti | 81 |
| 195 | 48.0 | 2343.8 | 1 | Ti/Ti | 75 |
| 73 | 47.5 | 2319.3 | 1 | Ti/Ti | 47 |
| 341 | 45.5 | 2221.7 | 1 | Ti/Ti | 67 |
| 117 | 44.0 | 2148.4 | 1 | ti/ti | 72 |
| 184 | 43.5 | 2t24.0 | 1 | ti/ti | 73 |
| 144 | 41.0 | 2002.0 | 1 | ti/ti | 81 |
| 58 | 41.0 | 2002.0 | 1 | ti/ti | 48 |
| 204 | 41.0 | 2002.0 | 1 | ti/ti | 69 |
| 330 | 40.5 | 1977.5 | 1 | ti/ti | 65 |
| 313 | 40.5 | 1977.5 | 1 | ti/ti | 70 |
| 262 | 40.0 | 1953.1 | 1 | ti/ti | 57 |
| 154 | 38.5 | 1879.9 | 1 | ti/ti | 78 |
| 203 | 37.5 | 1831.1 | 1 | ti/ti | 68 |
| 329 | 37.5 | 1831.1 | 1 | ti/ti | 69 |
| 247 | 35.5 | 1733.4 | 1 | ti/ti | 56 |
| 267 | 35.0 | 1709.0 | 1 | ti/ti | 54 |
| 108 | 35.0 | 1709.0 | 1 | ti/ti | 73 |
| 87 | 34.5 | 1684.6 | 1 | ti/ti | 72 |
| 49 | 32.0 | 1562.5 | 1 | ti/ti | 48 |
| 175 | 30.0 | 1464.8 | 9 | Ti/Ti | 46 |
| 71 | 30.0 | 1464.8 | 1 | ti/ti | 45 |
| 357 | 29.5 | 1440.4 | 1 | ti/ti | 70 |
| 57 | 23.0 | 1123.0 | 9 | Ti/Ti | 8 |
| 44 | 23.0 | 1123.0 | 9 | Ti/Ti | 14 |
| 384 | 22.5 | 1098.6 | 9 | Ti/Ti | 36 |
| 67 | 21.5 | 1049.8 | 9 | Ti/Ti | 15 |
| 24 | 21.5 | 1049.8 | 9 | Ti/Ti | 66 |
| 231 | 21.5 | 1049.8 | 9 | Ti/Ti | 47 |
| 220 | 21.0 | 1025.4 | 9 | Ti/Ti | 27 |
| 142 | 19.5 | 952.1 | 9 | Ti/Ti | 50 |
| 156 | 19.5 | 952.1 | 9 | Ti/Ti | 74 |
| 338 | 19.0 | 927.7 | 9 | Ti/Ti | 33 |
| 132 | 18.5 | 903.3 | 9 | Ti/Ti | 56 |
| 402 | 18.5 | 903.3 | 1 | ti/ti | 58 |
| 405 | 18.0 | 878.9 | 9 | Ti/Ti | 37 |
| 173 | 17.5 | 854.5 | 9 | Ti/Ti | 51 |
| 43 | 17.0 | 830.1 | 9 | Ti/Ti | 0 |
| 68 | 17.0 | 830.1 | 9 | Ti/Ti | 5 |
| 147 | 17.0 | 830.1 | 9 | Ti/Ti | 71 |
| 182 | 16.5 | 805.7 | 9 | Ti/Ti | 53 |
| 128 | 16.0 | 781.3 | 9 | Ti/Ti | 51 |
| 347 | i5.5 | 756.8 | 9 | ti/ti | 16 |
| 321 | 15.5 | 756.8 | 9 | ti/ti | 31 |
| 80 | 14.5 | 708.0 | 9 | ti/ti | 16 |
| 394 | 14.5 | 708.0 | 9 | ti/ti | 19 |
| 328 | 14.0 | 683.6 | 9 | ti/ti | 62 |
| 308 | 14.0 | 683.6 | 9 | ti/ti | 27 |
| 353 | 13.5 | 659.2 | 9 | ti/ti | 28 |
| 66 | 13.5 | 659.2 | 9 | ti/ti | 3 |
| 70 | 13.5 | 659.2 | 9 | ti/ti | 7 |
| 205 | 13.0 | 634.8 | 9 | ti/ti | 37 |
| 397 | 10.5 | 512.7 | 9 | ti/ti | 38 |
| 112 | 10.5 | 512.7 | 9 | ti/ti | 44 |
| 226 | 10.0 | 488.3 | 9 | ti/ti | 29 |
| 59 | 10.0 | 488.3 | 9 | ti/ti | 13 |
| 103 | 9.5 | 463.9 | 9 | ti/ti | 48 |
| 339 | 8.5 | 415.0 | 9 | ti/ti | 23 |
| 299 | 8.0 | 390.6 | 9 | ti/ti | 6 |
| 95 | 7.5 | 366.2 | 9 | ti/ti | 36 |
| 380 | 7.5 | 366.2 | 9 | ti/ti | 6 |
| 234 | 7.0 | 341.8 | 9 | ti/ti | 41 |
| 161 | 6.5 | 317.4 | 9 | ti/ti | 62 |
| 233 | 6.0 | 293.0 | 9 | ti/ti | 29 |
| 322 | 5.0 | 244.1 | 9 | ti/ti | 20 |
| 333 | 4.5 | 2i9.7 | 9 | ti/ti | 25 |
| 77 | 4.5 | 219.7 | 9 | ti/ti | 2 |
| 345 | 3.5 | 170.9 | 9 | ti/ti | 24 |
| 383 | 3.5 | i70.9 | 9 | ti/ti | 4 |

LSD = 423.19

TABLE 4

CORRELATION OF BNP, TRYPSIN AND CHYMOTRYPSIN FOR EXPERIMENTAL LINES FROM THE CROSS BX4P9341B6/KUNITZ
Correlation Coefficients/PROB>|R| Testing RHO = 0/Numner of Obs = 195

| Variable | BNP Score | TIU/gram | CIU/gram |
|---|---|---|---|
| BNP Score | 1.0000 | −0.8428 | −0.7170 |
| PROB>|R| | 0.0000 | 0.0000 | 0.0000 |
| TIU/gram | −0.8428 | 1.0000 | 0.7443 |
| PROB>|R| | 0.0000 | 0.0000 | 0.0000 |
| CIU/gam | −0.7170 | 0.7443 | 1.0000 |
| PROB>|R| | 0.0000 | 0.0000 | 0.0000 |

TABLE 5

AMINO ACID ANALYSIS

| Smpl # | Variety | BNP Score | TIU/ Gram | CYSI | ASPI | METI | THRI | SERI | GLUI | PRLI | GLYI |
|---|---|---|---|---|---|---|---|---|---|---|---|
| 17 | P9341 | 1 | 2935.11 | 0.42 | 3.34 | 0.90 | 1.14 | 1.59 | 5.66 | 1.19 | 1.09 |
| 19 | 8 | 1 | 2929.70 | 0.55 | 3.91 | 0.68 | 1.39 | 1.82 | 6.40 | 1.41 | 1.28 |
| 26 | 200 | 1 | 2832.00 | 0.33 | 3.00 | 0.80 | 1.00 | 1.44 | 4.86 | 1.07 | 1.11 |
| 9 | 279 | 1 | 2734.40 | 0.44 | 3.20 | 1.01 | 1.10 | 1.59 | 5.43 | 1.13 | 1.13 |

TABLE 5-continued

AMINO ACID ANALYSIS

| | | | | | | | | | | | |
|---|---|---|---|---|---|---|---|---|---|---|---|
| 10 | 164 | 1 | 2417.00 | 0.53 | 4.20 | 0.73 | 1.44 | 1.91 | 6.71 | 1.47 | 1.34 |
| 13 | KUNITZ | 1 | 2175.56 | 0.40 | 3.37 | 0.73 | 1.20 | 1.55 | 5.40 | 1.27 | 1.15 |
| 3 | 58 | 1 | 2002.00 | 0.59 | 4.02 | 0.96 | 1.45 | 1.89 | 6.57 | 1.52 | 1.30 |
| 8 | 204 | 1 | 2002.00 | 0.48 | 3.64 | 0.82 | 1.33 | 1.69 | 5.80 | 1.35 | 1.20 |
| 16 | 313 | 1 | 1977.50 | 0.45 | 3.32 | 0.78 | 1.24 | 1.57 | 5.38 | 1.24 | 1.09 |
| 18 | 154 | 1 | 1879.90 | 0.47 | 3.48 | 0.84 | 1.33 | 1.94 | 7.09 | 1.54 | 1.32 |
| 25 | 203 | 1 | 1831.10 | 0.49 | 3.83 | 0.87 | 1.39 | 1.80 | 6.17 | 1.44 | 1.25 |
| 11 | 108 | 1 | 1709.00 | 0.50 | 3.68 | 0.93 | 1.23 | 1.75 | 6.20 | 1.42 | 1.22 |
| 14 | BX4P9341B6 | 9 | 1177.30 | 0.43 | 3.55 | 1.29 | 1.23 | 1.73 | 6.16 | 1.38 | 1.19 |
| 24 | 384 | 9 | 1098.60 | 0.54 | 3.87 | 0.93 | 1.33 | 1.69 | 6.09 | 1.45 | 1.24 |
| 5 | 24 | 9 | 1049.80 | 0.47 | 3.50 | 0.80 | 1.30 | 1.62 | 5.58 | 1.33 | 1.18 |
| 22 | 220 | 9 | 1025.40 | 0.40 | 3.46 | 1.23 | 1.17 | 1.66 | 6.03 | 1.33 | 1.12 |
| 27 | 405 | 9 | 878.90 | 0.49 | 4.10 | 1.44 | 1.40 | 1.95 | 7.20 | 1.61 | 1.36 |
| 21 | 353 | 9 | 659.20 | 0.41 | 3.48 | 1.25 | 1.15 | 1.68 | 6.07 | 1.33 | 1.11 |
| 20 | 339 | 9 | 415.00 | 0.51 | 3.95 | 1.53 | 1.29 | 1.87 | 6.91 | 1.52 | 1.24 |
| 2 | 299 | 9 | 390.60 | 0.43 | 3.42 | 1.22 | 1.18 | 1.54 | 5.56 | 1.28 | 1.18 |
| 23 | 233 | 9 | 293.00 | 0.54 | 3.98 | 0.90 | 1.45 | 1.82 | 6.42 | 1.48 | 1.33 |
| 4 | 322 | 9 | 244.10 | 0.58 | 3.38 | 0.96 | 1.22 | 1.55 | 5.32 | 1.23 | 1.16 |
| 15 | 345 | 9 | 170.90 | 0.41 | 3.04 | 1.17 | 1.07 | 1.49 | 5.12 | 1.20 | 1.11 |

| Smpl # | ALAI | VALI | ILEI | LEUI | TYRI | PHEI | HISI | LYSI | AGRI | S-containing |
|---|---|---|---|---|---|---|---|---|---|---|
| 17 | 1.23 | 1.40 | 1.39 | 2.44 | 1.26 | 1.62 | 0.72 | 1.94 | 2.87 | 1.32 |
| 19 | 1.37 | 1.65 | 1.56 | 2.68 | 1.34 | 1.78 | 0.81 | 2.10 | 2.64 | 1.23 |
| 26 | 1.06 | 1.26 | 1.20 | 2.11 | 1.11 | 1.35 | 0.67 | 1.72 | 2.31 | 1.13 |
| 9 | 1.16 | 1.39 | 1.30 | 2.28 | 1.19 | 1.48 | 0.70 | 1.85 | 2.48 | 1.45 |
| 10 | 1.44 | 1.74 | 1.67 | 2.81 | 1.40 | 1.89 | 0.85 | 2.31 | 2.82 | 1.27 |
| 13 | 1.19 | 1.45 | 1.37 | 2.30 | 1.16 | 1.51 | 0.73 | 1.95 | 2.28 | 1.13 |
| 3 | 1.39 | 1.70 | 1.62 | 2.72 | 1.42 | 1.82 | 0.86 | 2.31 | 2.72 | 1.54 |
| 8 | 1.31 | 1.52 | 1.50 | 2.52 | 1.27 | 1.63 | 0.77 | 2.12 | 2.44 | 1.31 |
| 16 | 1.20 | 1.42 | 1.37 | 2.34 | 1.18 | 1.53 | 0.71 | 1.90 | 2.17 | 1.23 |
| 18 | 1.35 | 1.70 | 1.66 | 2.93 | 1.41 | 1.89 | 0.86 | 2.22 | 3.29 | 1.31 |
| 25 | 1.36 | 1.59 | 1.54 | 2.68 | 1.35 | 1.76 | 0.79 | 2.16 | 2.53 | 1.36 |
| 11 | 1.29 | 1.44 | 1.39 | 2.57 | 1.21 | 1.63 | 0.78 | 2.02 | 3.23 | 1.43 |
| 14 | 1.27 | 1.52 | 1.46 | 2.61 | 1.31 | 1.67 | 0.80 | 2.03 | 2.86 | 1.73 |
| 24 | 1.34 | 1.62 | 1.59 | 2.64 | 1.29 | 1.71 | 0.76 | 2.13 | 2.49 | 1.47 |
| 5 | 1.26 | 1.56 | 1.46 | 2.44 | 1.22 | 1.60 | 0.74 | 2.02 | 2.30 | 1.27 |
| 22 | 1.22 | 1.47 | 1.43 | 2.55 | 1.27 | 1.68 | 0.78 | 1.96 | 2.87 | 1.63 |
| 27 | 1.41 | 1.80 | 1.70 | 2.96 | 1.46 | 1.91 | 0.91 | 2.35 | 3.39 | 1.93 |
| 21 | 1.20 | 1.50 | 1.47 | 2.60 | 1.22 | 1.67 | 0.76 | 1.96 | 2.76 | 1.66 |
| 20 | 1.34 | 1.63 | 1.59 | 2.87 | 1.39 | 1.87 | 0.87 | 2.15 | 3.39 | 2.04 |
| 2 | 1.25 | 1.48 | 1.40 | 2.48 | 1.23 | 1.61 | 0.73 | 1.91 | 2.83 | 1.64 |
| 23 | 1.45 | 1.74 | 1.63 | 2.77 | 1.39 | 1.80 | 0.85 | 2.36 | 2.85 | 1.44 |
| 4 | 1.19 | 1.46 | 1.39 | 2.31 | 1.21 | 1.55 | 0.74 | 1.97 | 2.26 | 1.54 |
| 15 | 1.05 | 1.30 | 1.22 | 2.15 | 1.11 | 1.38 | 0.77 | 1.89 | 2.49 | 1.58 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

What claimed is:

1. A soybean seed obtained by crossing:
    a) a first soybean plant having reduced trypsin and/or chymotrypsin inhibitor activity relative to a wild type of the plant species and
    b) a second soybean plant that is transformed to preferentially express a preselected protein, whereby the content of trypsin and/or chymotrypsin inhibitor is diminished in the seed,
wherein the preselected protein accumulates in the seed and is rich in methionine.

2. The seed of claim 1 wherein the protease inhibitor whose content is diminished in the seed is selected from the group consisting of a Kunitz inhibitor, a Bowman-Birk inhibitor and a glycine-rich soybean trypsin inhibitor.

3. The seed of claim 1 wherein the first preselected protein is Brazil nut protein.

4. A method of reducing the level of trypsin and/or chymotrypsin inhibitor in soybean seeds comprising crossing:
    a) a first soybean plant having reduced trypsin and/or chymotrypsin inhibitor activity relative to a wild type soybean plant and
    b) a second soybean plant that is transformed to preferentially express a preselected protein whereby the content of trypsin and/or chymotrypsin inhibitor is diminished in the seed,
wherein the preselected protein accumulates in the seed and is rich in methionine.

5. The method of claim 4 wherein the protease inhibitor is selected from the group consisting of a Kunitz inhibitor, a Bowman-Birk inhibitor and a glycine-rich soybean trypsin inhibitor.

6. The method of claim 4 wherein the first preselected protein is Brazil nut protein.

7. The method of claim 4 wherein the first preselected protein is a methionine-rich protein.

8. A method of producing feed that can be fed to animals in a raw form comprising producing soybean seeds by crossing:

a) a first soybean plant having reduced trypsin and/or chymotrypsin inhibitor activity relative to a wild type of the plant species and b) a second soybean plant that is transformed to preferentially express a preselected protein whereby the content of trypsin and/or chymotrypsin inhibitor is diminished in the seed, wherein the preselected protein accumulates in the seed and is rich in methionine.

9. The method of claim 8 wherein the protease inhibitor is selected from the group consisting of a Kunitz inhibitor, a Bowman-Birk inhibitor and a glycine-rich soybean trypsin inhibitor.

10. The method of claim 8 wherein the first preselected protein is Brazil nut protein.

11. The method of claim 8 wherein the feed produced is poultry feed.

12. The seed of claim 1 wherein the plant in step a) is a mutant.

13. The method of claim 4 wherein the plant in step a) is a mutant.

14. The method of claim 8 wherein the plant in step a) is a mutant.

* * * * *